US012758401B2

(12) United States Patent
Chapman et al.

(10) Patent No.: US 12,758,401 B2
(45) Date of Patent: Oct. 13, 2026

(54) ORTHOPEDIC LEG ALIGNMENT SYSTEM AND METHOD

(71) Applicant: Howmedica Osteonics, Corp, Mahwah, NJ (US)

(72) Inventors: Ryan M. Chapman, North Hartland, VT (US); Doug W. Van Citters, Hanover, NH (US); Gordon Goodchild, Coral Springs, FL (US)

(73) Assignee: Howmedica Osteonics, Corp

( * ) Notice: Subject to any disclaimer, the term of this patent is extended or adjusted under 35 U.S.C. 154(b) by 0 days.

(21) Appl. No.: 18/809,795

(22) Filed: Aug. 20, 2024

(65) Prior Publication Data

US 2024/0407932 A1 Dec. 12, 2024

Related U.S. Application Data

(63) Continuation of application No. 18/312,922, filed on May 5, 2023, now Pat. No. 12,097,130, which is a continuation of application No. 16/994,456, filed on Aug. 14, 2020, now Pat. No. 11,679,007, which is a continuation of application No. 15/449,892, filed on Mar. 3, 2017, now Pat. No. 10,828,175.

(60) Provisional application No. 62/302,953, filed on Mar. 3, 2016.

(51) Int. Cl.
*A61F 2/46* (2006.01)
*A61F 2/30* (2006.01)
*A61F 2/38* (2006.01)

(52) U.S. Cl.
CPC ............ *A61F 2/4684* (2013.01); *A61F 2/389* (2013.01); *A61F 2/4657* (2013.01); *A61F 2/468* (2013.01); *A61F 2002/30953* (2013.01); *A61F 2002/4666* (2013.01); *A61F 2002/4668* (2013.01)

(58) Field of Classification Search
CPC ............ A61F 2/4657; A61F 2002/4658; A61F 2002/4668; A61F 2/4684
See application file for complete search history.

(56) References Cited

U.S. PATENT DOCUMENTS

| | | | | |
|---|---|---|---|---|
| 7,195,645 | B2 * | 3/2007 | Disilvestro | A61B 5/076 600/587 |
| 7,481,780 | B2 | 1/2009 | de Guise et al. | |
| 7,594,933 | B2 | 9/2009 | Kammerzell | |
| 8,421,642 | B1 | 4/2013 | McIntosh et al. | |
| 8,494,805 | B2 | 7/2013 | Roche et al. | |
| 8,814,877 | B2 | 8/2014 | Wasielewski | |
| 9,125,678 | B2 | 9/2015 | Lye | |
| 9,138,319 | B2 | 9/2015 | Fanson | |

(Continued)

*Primary Examiner* — Matthew J Lawson
(74) *Attorney, Agent, or Firm* — Bookoff McAndrews, PLLC

(57) ABSTRACT

An orthopedic measurement system system includes a tri-axial gyroscope configured to measure movement of a leg. The gyroscope can be placed in an insert or tibial prosthetic component that couples to the tibia. The gyroscope may be used to measure alignment relative to the mechanical axis of the leg. The leg alignment measurement may be performed by putting the leg through a first leg movement and a second leg movement. The gyroscope outputs angular velocities on the axes that the sensor is rotated about. The gyroscope may be coupled to a computer that calculates the alignment of the leg relative to the mechanical axis from the gyroscope measurement data.

18 Claims, 10 Drawing Sheets

(56) References Cited

U.S. PATENT DOCUMENTS

| | | | | |
|---|---|---|---|---|
| 9,259,172 | B2 | 2/2016 | Stein | |
| 9,271,756 | B2 | 3/2016 | van der Walt | |
| 9,649,160 | B2 | 5/2017 | van der Walt et al. | |
| 9,820,678 | B2 | 11/2017 | Stein et al. | |
| 2004/0243148 | A1 | 12/2004 | Wasielewski | |
| 2005/0010299 | A1* | 1/2005 | Disilvestro | A61F 2/32 600/587 |
| 2006/0271199 | A1 | 11/2006 | Johnson | |
| 2009/0138019 | A1 | 5/2009 | Wasielewski | |
| 2010/0204575 | A1* | 8/2010 | Roche | A61B 8/58 367/127 |
| 2010/0249791 | A1* | 9/2010 | Roche | A61F 2/4657 606/86 R |
| 2011/0160738 | A1* | 6/2011 | McIntosh | A61B 34/20 606/102 |
| 2011/0275957 | A1 | 11/2011 | Bhandari | |
| 2012/0277752 | A1 | 11/2012 | Wasielewski | |
| 2012/0323834 | A1* | 12/2012 | Fujimaki | G06N 7/01 706/46 |
| 2013/0053856 | A1 | 2/2013 | Penenberg | |
| 2013/0190887 | A1 | 7/2013 | Fanson | |
| 2013/0310841 | A1* | 11/2013 | Fitz | A61B 5/1072 606/102 |
| 2014/0107471 | A1 | 4/2014 | Haider | |
| 2014/0135773 | A1 | 5/2014 | Stein | |
| 2014/0276241 | A1 | 9/2014 | Stein | |
| 2014/0276862 | A1 | 9/2014 | Stein | |
| 2014/0276864 | A1* | 9/2014 | Aghazadeh | A61F 2/4657 606/88 |
| 2014/0276871 | A1 | 9/2014 | Sherman | |
| 2014/0276888 | A1 | 9/2014 | Stein | |
| 2014/0288464 | A1* | 9/2014 | Stein | A61F 2/4657 600/595 |
| 2014/0303539 | A1 | 10/2014 | Baym | |
| 2014/0330112 | A1 | 11/2014 | Wasielewski | |
| 2015/0142372 | A1 | 5/2015 | Singh | |
| 2015/0272696 | A1 | 10/2015 | Fry | |
| 2015/0313684 | A1 | 11/2015 | Fanson | |
| 2015/0342516 | A1* | 12/2015 | Nguyen | A61B 34/10 606/102 |
| 2016/0157940 | A1 | 6/2016 | Stein | |
| 2016/0367382 | A1* | 12/2016 | Zaima | A61F 2/4657 |

* cited by examiner

ORTHOPEDIC LEG ALIGNMENT SYSTEM AND METHOD

CROSS-REFERENCE TO RELATED APPLICATION(S)

This patent application is a continuation of and claims the benefit of priority to U.S. application Ser. No. 18/312,922, filed May 5, 2023, which is a continuation of U.S. application Ser. No. 16/994,456, filed on Aug. 14, 2020, now U.S. Pat. No. 11,679,007, issued Jun. 20, 2023, which is a continuation of U.S. application Ser. No. 15/449,892, filed Mar. 3, 2017, now U.S. Pat. No. 10,828,175, issued Nov. 10, 2020, which claims priority to U.S. Provisional Application No. 62/302,953, filed Mar. 3, 2016, all of which are incorporated herein by reference in their entireties.

FIELD

The present invention pertains generally to measurement of physical parameters, and particularly to, but not exclusively to, measuring orthopedic alignment.

BACKGROUND

The musculoskeletal system of a mammal is subject to variations among species. Further changes can occur due to environmental factors, degradation through use, and aging. A joint of the musculoskeletal system typically comprises two or more bones that move in relation to one another. Movement is enabled by muscle tissue and tendons that is a part of the musculoskeletal system. Ligaments can position, hold, and stabilize one or more bones of a joint. Cartilage is a wear surface that prevents bone-to-bone contact, distributes load, and lowers friction.

There has been substantial growth in the repair of the human musculoskeletal system. In general, prosthetic joints have evolved using information from simulations, mechanical prototypes, and patient data that is collected and used to initiate improved designs. Similarly, the tools being used for orthopedic surgery have been refined over the years but have not changed substantially. Thus, the basic procedure for correction of the musculoskeletal system has been standardized to meet the general needs of a wide distribution of the population. Although the tools, procedure, and artificial replacement systems meet a general need, each replacement procedure is subject to significant variation from patient to patient. The correction of these individual variations relies on the skill of the surgeon to adapt and fit the replacement joint using the available tools to the specific circumstance. It would be of great benefit if a system could be developed that improves surgical outcomes and reduces the cost and time of a surgery.

BRIEF DESCRIPTION OF THE DRAWINGS

Various features of the system are set forth with particularity in the appended claims. The embodiments herein, can be understood by reference to the following description, taken in conjunction with the accompanying drawings, in which:

DETAILED DESCRIPTION

Figure 1:
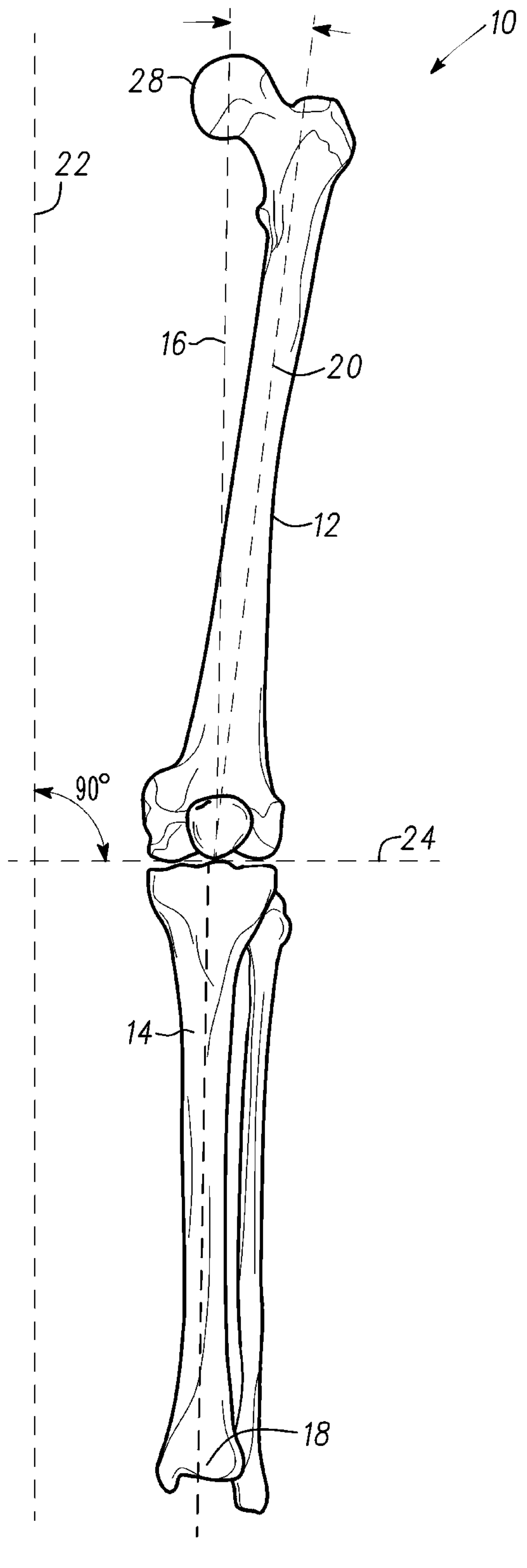
FIG. 1 is an illustration of a leg in accordance with an example embodiment.

Embodiments of the invention are broadly directed to measurement of physical parameters, and more particularly, to a system that supports accurate measurement, improves surgical outcomes, reduces cost, reduces time in surgery.

The following description of exemplary embodiment(s) is merely illustrative in nature and is in no way intended to limit the invention, its application, or uses.

Processes, techniques, apparatus, and materials as known by one of ordinary skill in the art may not be discussed in detail but are intended to be part of the enabling description where appropriate. For example specific computer code may not be listed for achieving each of the steps discussed, however one of ordinary skill would be able, without undo experimentation, to write such code given the enabling disclosure herein. Such code is intended to fall within the scope of at least one exemplary embodiment.

In all of the examples illustrated and discussed herein, any specific materials, such as temperatures, times, energies, and material properties for process steps or specific structure implementations should be interpreted to be illustrative only and non-limiting. Processes, techniques, apparatus, and materials as known by one of ordinary skill in the art may not be discussed in detail but are intended to be part of an enabling description where appropriate. It should also be noted that the word "coupled" used herein implies that elements may be directly coupled together or may be coupled through one or more intervening elements.

Additionally, the sizes of structures used in exemplary embodiments are not limited by any discussion herein (e.g., the sizes of structures can be macro (centimeter, meter, and larger sizes), micro (micrometer), and nanometer size and smaller).

Notice that similar reference numerals and letters refer to similar items in the following figures, and thus once an item is defined in one figure, it may not be discussed or further defined in the following figures.

In general, prosthesis is an artificial body part. An orthopedic implant is a device used to repair the musculoskeletal system. Common examples of an orthopedic implant are pins, rods, screws, cages, plates and other devices that typically couple to bone of the musculoskeletal system. A prosthetic joint can be part of a system that supports movement of the musculoskeletal system. A prosthetic joint typically comprises several prosthetic components that combine to mimic a natural joint. For example, a prosthetic hip joint comprises an acetabular shell, an acetabular bearing, and a femoral prosthetic component. The acetabular shell couples to the pelvis and is a pivot point of the joint. The acetabular bearing fits in the acetabular shell and provides a bearing surface that supports hip movement. The femoral prosthetic component comprises a femoral head and a femoral hip stem. The head couples to the hip stem and fits into the acetabular bearing to distribute loading to the bearing surface. The femoral hip stem couples to the proximal end of the femur. Thus, a prosthetic hip joint is a ball and socket joint that couples the femur to the pelvis to support movement of the leg. Similarly, prosthetic components are available to repair the knee, ankle, shoulder, hand, fingers, wrist, toes, spine and other areas of the musculoskeletal system.

The prosthetic joint or a prosthetic component of the joint can also have a number of sensors for generating measurement data related to the installation. For example, joint position or prosthetic component loading can be monitored in surgery or long-term. A result of the monitoring could be that an exercise regimen could be prescribed to improve the range of motion. Similarly, balance, loading, alignment, or joint position could be monitored or data stored to study kinematics of the joint or provide a kinetic assessment of the joint.

FIG. 1 is an illustration of a leg 10 in accordance with an example embodiment. Leg 10 can be a right or left leg. Leg 10 comprises a femur 12 and a tibia 14. A dashed line 16 illustrates a mechanical axis of leg 10. The mechanical axis of leg 10 comprises dashed line 16 drawn through a center of a femoral head 28 to a center of ankle joint 18. Dashed line 16 aligns through a center of a knee joint at approximately the medial tibial spine. The knee joint comprises lateral and medial articular surfaces that support leg movement. Alignment of leg 10 to the mechanical axis minimizes wear on articular surfaces of a prosthetic knee joint and reduces mechanical stress on the wear surfaces. Similarly, alignment to the mechanical axis of leg 10 reduces stress on the prosthetic components coupled to femur 12 and tibia 14. Alignment of the knee joint further includes balancing between the lateral and medial compartments of the knee joint.

A dashed line 22 is a vertical axis that is drawn relative to the mechanical axis and an anatomical axis. A dashed line 24 is a horizontal axis that is perpendicular to vertical axis 22. The horizontal axis is shown drawn between a distal end of femur 12 and a proximal end of tibia 14. The vertical axis aligns with the pubic symphysis which is a midline cartilaginous joint in proximity to a pelvic region. The anatomical axis is illustrated by dashed line 20. The anatomical axis is not a straight line as it traverses an intramedullary canal of femur 12 and an intramedullary canal of tibia 14. The mechanical axis and the anatomical axis are the same from the knee joint to the center of the ankle of the leg. Both the mechanical axis and the anatomical axis differ from the vertical axis.

The femur 12 and tibia 14 can be misaligned to the mechanical axis of the leg. In an aligned leg, the mechanical axis forms an angle of approximately 3 degrees with the vertical axis. Similarly, in an aligned leg, femur 12 of the anatomical axis forms a 5-7 degree angle with the mechanical axis. Ideally, a surgeon installs prosthetic components of the knee joint aligned to the mechanical axis of the leg to optimize reliability and performance of the knee joint. The alignment process can include measurement of leg misalignment and compensation to keep alignment of the leg to the mechanical axis within a predetermined range. Typically, the predetermined range is determined by a prosthetic component manufacturer based on clinical evidence that supports reliability and performance of the joint when misalignment is kept within the predetermined range. Mechanical jigs have been used to measure leg alignment in the operating room. The mechanical jigs can be cumbersome, take time to set up, and can be inaccurate. One issue with mechanical jigs is that the center of the femoral head is not available for direct measurement by the jigs. In the case of a leg deformity a surgeon may require an alignment offset from the mechanical axis. In general, leg alignment can be adjusted through bone cuts, prosthetic component rotation, ligament tensioning, prosthetic component shimming, and other techniques during a trial installation. In one embodiment, a real-time alignment measurement system uses a tri-axial gyroscope or three separate gyroscopes to provide alignment measurement data during trialing of prosthetic components. The alignment measurement data can be used to verify alignment or to support change that places the leg in alignment.

Figure 2:
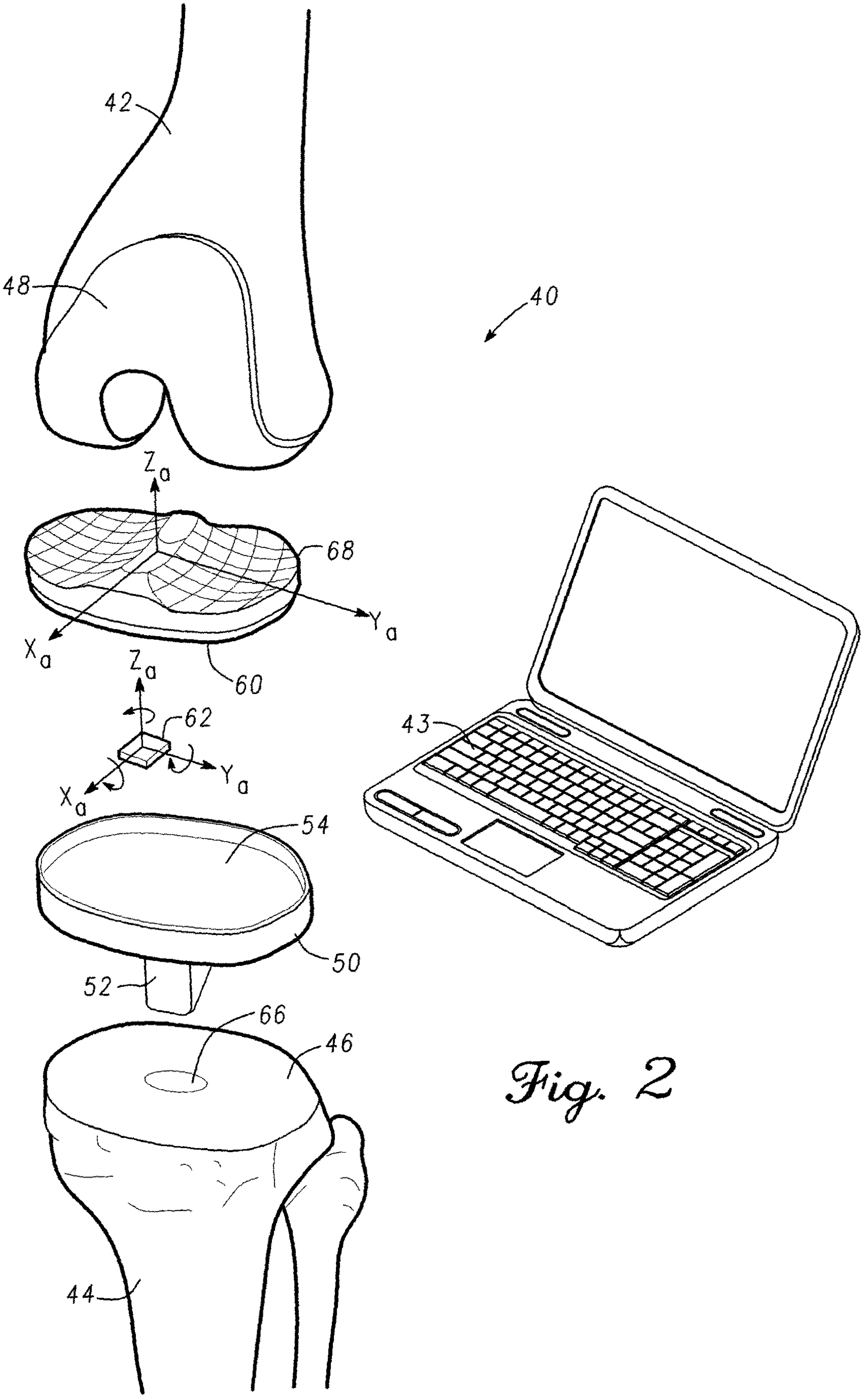
FIG. 2 is an exploded view of a prosthetic knee joint in accordance with an example embodiment configured to measure alignment of a leg.

FIG. 2 is an exploded view of a prosthetic knee joint 40 in accordance with an example embodiment configured to measure alignment of a leg. The prosthetic knee joint comprises a femoral prosthetic component 48 coupled to a distal end of a femur 42, an insert 58, and a tibial prosthetic component 50 coupled to a proximal end of a tibia 44. A tri-axial gyroscope 62 is coupled to the knee joint to support real-time alignment measurement. In one embodiment, tri-axial gyroscope 62 is coupled to tibia 44. Tri-axial gyroscope 62 comprises three gyroscopes where a first, second, and third gyroscope is respectively aligned to X, Y, and Z axes. Each gyroscope measures an angular velocity corresponding to an axis as indicated on the diagram. Alternatively, three separate gyroscopes can also be used to measure leg alignment each gyroscope respectively aligned to a corresponding axis as shown.

The proximal end of tibia 44 has a prepared bone surface 46. Prepared bone surface 46 of tibia 44 is cut relative to a reference. For example, the proximal end of tibia 44 can be cut relative to the transepicondylar axis. Alternatively, there are other references that can also be used. Bone cuts to the femur and tibia can also be made referenced to the vertical axis, mechanical axis, or anatomical axis. Prepared bone surface 46 can have a medial-lateral slope, anterior-posterior slope or a compound slope that supports accurate leg movement and proper rotation of femoral component 48 over a range of motion.

Tibial prosthetic component 50 includes an upper surface 54 and a bottom surface 56. In one embodiment, upper surface 54 is a major surface of a tibial tray. The tibial tray supports and retains insert 58 to tibial prosthetic component 50. Tibial prosthetic component 50 can have one or more retaining features for coupling to prepared bone surface 46. In one embodiment, tibial prosthetic component 50 has a keel 52 that inserts into an opening 66 drilled into tibia 44. Opening 66 defines a location of tibial prosthetic component 50 on prepared bone surface 46. Keel 52 positions, retains, and strengthens coupling of tibial prosthetic component 50 to tibia 44. Tibial prosthetic component 50 can be rotated from a reference position. In one embodiment, a position of tibial prosthetic component 50 on tibia 44 is referenced to a medial third of the tibia tubercle. Rotation of tibial prosthetic component 50 from this reference position can be measured and provided to the alignment measurement system. For example, rotation can be used to affect movement of the patella to femoral prosthetic component 48. Rotation of tibial prosthetic component 50 can also be used to affect alignment, balance, and contact point of femoral prosthetic component 48 to insert 50. Once the position of tibial prosthetic component 50 is determined bottom surface 56 of tibial prosthetic component 50 can be coupled to prepared bone surface 46 to further retain tibial prosthetic component 50 to tibia 44. Coupling of tibial prosthetic component 50 to tibia 44 typically comprises a mechanical attachment, an adhesive, or cement.

Bottom surface 56 of tibial prosthetic component 50 couples to prepared bone surface 46. In one embodiment, bottom surface 56 is approximately parallel to prepared bone surface 46. Similarly, upper surface 54 of tibia prosthetic component 50 is parallel to bottom surface 56 or prepared bone surface 46. A surface 60 of insert 58 couples to upper surface 54 of tibial prosthetic component 50. Insert 58 can have one or more retaining features that couple to tibial prosthetic component 50. Surface 60 of insert 58 is parallel to upper surface 54 of tibial prosthetic component 50.

In one embodiment, tri-axial gyroscope 62 is a MEMs (micro-electro mechanical) integrated circuit. The form factor of a MEMs gyroscope integrated circuit supports placement in a prosthetic component or coupling to a prosthetic component to measure alignment of the muscular-skeletal system. A MEMs gyroscope is a solid state device formed using a photolithographic process. The MEMs gyroscope has a form factor that supports placement within a prosthetic component or a module that can be coupled to a bone surface. In one embodiment, MEMs gyroscope has a resonating mass that shifts when angular velocity changes and outputs a signal corresponding to the angular velocity change. MEMs gyroscopes can provide an analog or digital output. In one embodiment, measurement data from tri-axial gyroscope 62 is transmitted to a computer 43 configured to process and display alignment information of the leg. Typically, tri-axial gyroscope 62 includes a mounting surface. The mounting surface can correspond to a plane of two of the axes of tri-axial gyroscope 62. In one embodiment, the X-Y plane of tri-axial gyroscope 62 is placed parallel to prepared bone surface 46 of tibia 44 and corresponding parallel surfaces of tibial prosthetic component 50 and insert 58. In one embodiment, tri-axial gyroscope 62 is placed in a trial insert. The trial insert is used to support installation of a prosthetic knee joint. The trial insert with tri-axial gyroscope 62 can measure alignment of the leg and support changes or modifications prior to final installation to ensure alignment is within a predetermined range for optimal performance and reliability. The trial insert can also include other sensors to provide measurement data on other parameters in proximity to the leg or to support installation of the prosthetic components. Tri-axial gyroscope 62 can also be placed in other prosthetic components or a module. For example, tri-axial gyroscope 62 can be placed in a final insert or a final tibial prosthetic component to perform alignment measurements long-term or monitor changes in alignment. As disclosed herein above, the position of tibial prosthetic component 50 can be aligned or referenced to the medial third of the tibia tubercle. The orientation of insert 58 corresponds to the position of tibial prosthetic component 50. Insert 58 incorporating tri-axial gyroscope 62 is placed having the X-axis aligned to an anterior-posterior direction of insert 58 and the Y-axis aligned to the medial-lateral direction of insert 58.

Figure 3:
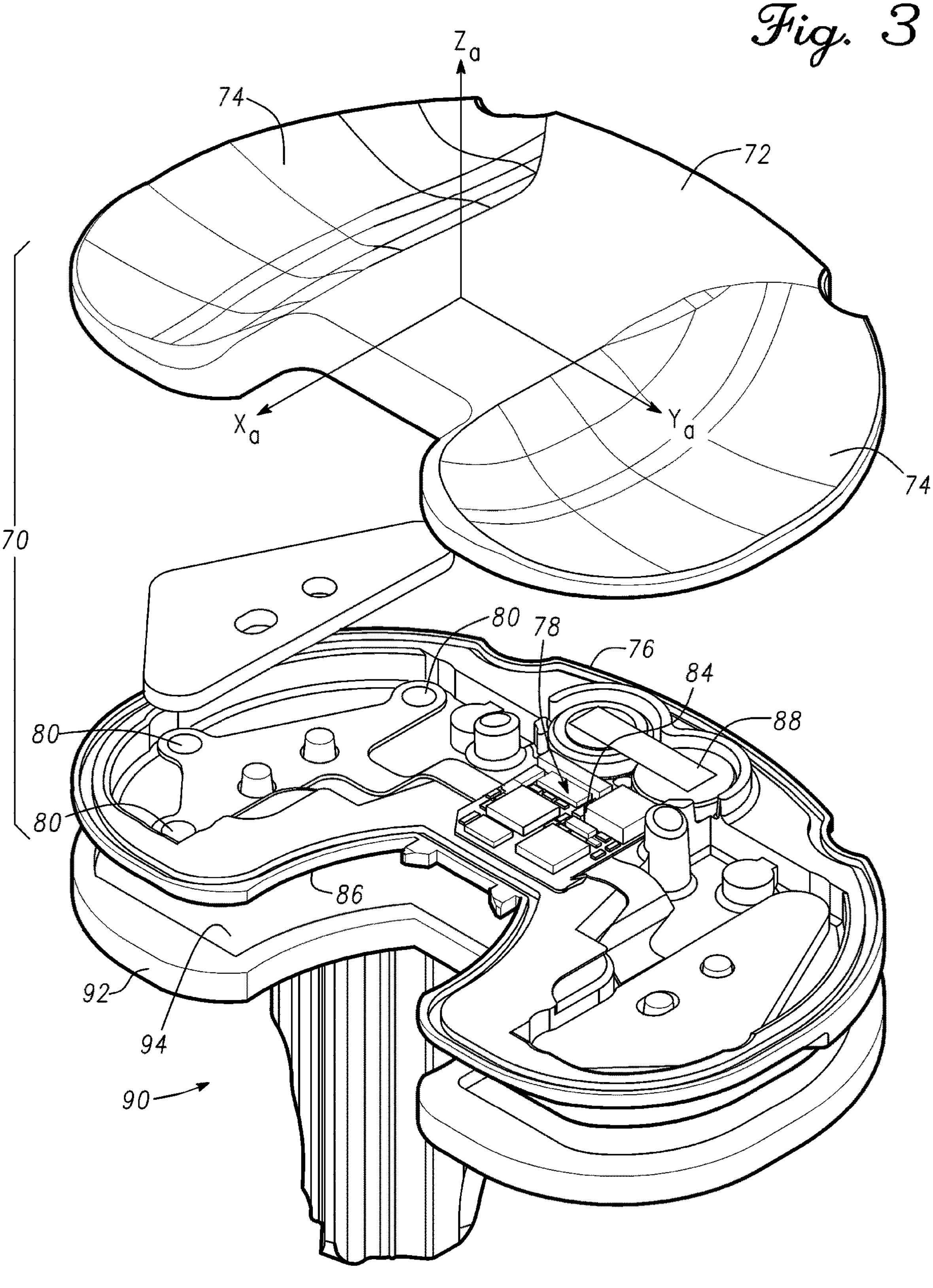
FIG. 3 is an illustration of a prosthetic component incorporating a tri-axial gyroscope in accordance with an example embodiment.

FIG. 3 is an illustration of a prosthetic component incorporating a tri-axial gyroscope 82 in accordance with an example embodiment. In general, the tri-axial gyroscope 82 can be housed in a prosthetic component 70 or coupled to the muscular-skeletal system to measure alignment. Tri-axial gyroscope 82 can measure alignment of the muscular-skeletal system or measure bone position. Tri-axial gyroscope 82 can have a predetermined orientation referenced to the prosthetic component. The prosthetic component can be a trialing device that is a temporary device used during installation for measuring parameters and determining appropriate fit of the prosthetic joint. The prosthetic component can also be a permanent prosthetic component that monitors or measures alignment long-term. For example, changes in alignment over time can indicate incorrect loading on the articular surfaces that long-term could accelerate wear if not corrected. Although tri-axial gyroscope 82 is placed in a knee joint it is not limited to knee prosthetic components and can be applied similarly to other parts of the anatomy such as but not limited to the muscular-skeletal system, hip, shoulder, spine, ankle, elbow, wrist, fingers, toes, and wrist. Similarly, tri-axial gyroscope 82 can be placed in other knee components such as a patellar button, tibial prosthetic component, or femoral prosthetic component to support alignment measurement or other measurements.

In one embodiment, insert 70 comprises a support structure 72 having articular surfaces 74 and a support structure 76. Support structures 72 and 76 couple together to form a housing. The housing includes at least one cavity for electronic circuitry and sensors. In one embodiment, a peripheral surface of support structure 72 couples to a peripheral surface of support structure 76. The surfaces can be coupled together via an adhesive that seals the cavity from the external environment. The interior and exterior of insert 70 can be sterilized and stored in a package prior to use. Support structures 72 and 76 comprise a bio-compatible polymer such as polycarbonate, PEEK, or ultrahigh molecular weight polyethylene. The selected polymer can support loading applied by the muscular-skeletal system while providing a low friction surface for joint movement and reduced wear.

A measurement system comprises tri-axial gyroscope 82, sensors, electronic circuitry 78, a power source 88, and a remote system. Tri-axial gyroscope 82, sensors, electronic circuitry 78, and power source 88 are housed in insert 70. The remote system is placed in proximity to insert 70. For example, the remote system can be placed in an operating room in a location that allows the surgical team to view measurement data provided by the sensors and tri-axial gyroscope 82. The remote system receives measurement data from the sensors and tri-axial gyroscope 82 via wired connection or wireless transmission. Typically, wireless transmission is short range, usually less than 10 meters and can be encrypted for security. The remote system can comprise a computer with a display to receive and process measurement data from insert 70. The computer can include software programs to support calculation and visualization of the measurement data. In one embodiment, the measurement data can be displayed to the surgeon in real-time allowing changes to be made based on the quantitative measurements. Alternatively, the remote system can be a microprocessor based device capable of running software such as a smart phone or handheld device that allows a patient to review measurement data transmitted from the prosthetic component.

Insert 70 couples to a tibial prosthetic component 90. Tibial prosthetic component 90 couples to a tibia and includes a tibial tray 92 that retains insert 70. Tibial tray 92 includes a surface 94 to which bottom surface 86 of structure 76 couples. Articular surfaces 74 couple to condyles of a femoral prosthetic component to support movement of the knee joint and the leg. Load sensors 80 can be placed underlying articular surfaces 74. The measurement system can measure load and position of load applied to articular surfaces 74. The load applied to articular surfaces 74 is distributed to a bottom surface 86 of support structure 76 that couples to a tibial prosthetic component 90. The surface area of bottom surface 86 is greater in area than the condyle contact area of the femoral prosthetic component to articular surfaces 74. The measurement system also includes tri-axial gyroscope 82 for measuring alignment of a leg relative to a mechanical axis of the leg. The tri-axial gyroscope comprises three gyroscopes. A first gyroscope has a rotational axis aligned in an anterior-posterior direction of insert 70 corresponding to an axis X. A second gyroscope has a rotational axis aligned in a medial-lateral direction of insert 70 corresponding to an axis Y. A third gyroscope has a rotational axis perpendicular to an X-Y plane corresponding to an axis Z.

Electronic circuitry 78 can be housed in the prosthetic component with tri-axial gyroscope 82 aligned as stated above or in another predetermined alignment. Alternatively, three separate gyroscopes can be used and aligned in the predetermined alignment. As mentioned tri-axial gyroscope 82 is a small form factor device that allows placement within the prosthetic component or device that couples to the muscular-skeletal system. The sensors can measure a parameter of the musculoskeletal system or measure a parameter in proximity to insert 70.

Electronic circuitry 78 is mounted on a printed circuit 84 that is centrally mounted in the cavity of insert 70. Electronic circuitry 78 is mounted in an area of insert 70 that has little or no joint loading for reliability. Load sensors 80 couple to electronic circuitry 78 and underlie articular surfaces 74. In one embodiment, load sensors 80 and electronic circuitry 78 are coupled to a flexible and unitary printed circuit board. In one embodiment, load sensors 80 can be integrated into the printed circuit board to simplify assembly, improve reliability, and increase performance of the measurement system. Three or more load sensors 80 are used measure a position where the load is applied on articular surfaces 74. A tri-axial gyroscope 82 is mounted to printed circuit board 84 and couples to electronic circuitry 78. Tri-axial gyroscope 82 is mounted such that the three gyroscopes are oriented in relation to the prosthetic component. In one embodiment, the X-Y plane of tri-axial gyroscope 82 is parallel to bottom surface 86 of insert 70 and surface 94 of tibial prosthetic component 90.

Electronic circuitry 78 and tri-axial gyroscope 82 are isolated from an external environment when support structure 72 is coupled to support structure 76 of FIG. 3. Electronic circuitry 78 can include a power source 88, passive components, power regulation, power management circuitry, conversion circuitry, digital logic, analog circuitry, microprocessors, microcontrollers, digital signal processors, memory, ASICs, interface circuitry, or communication circuitry. In one embodiment, tri-axial gyroscope 82 provides measurement data in real-time to a computer via radio frequency wireless transmission.

Figure 4:
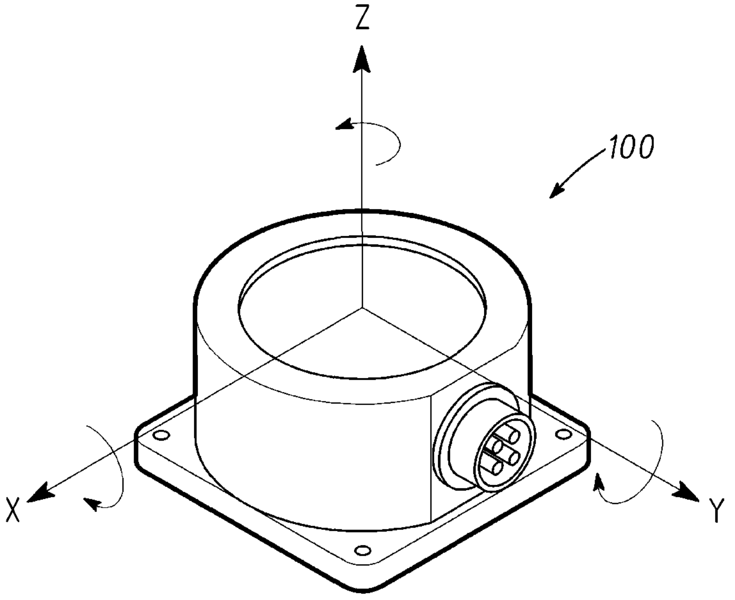
FIG. 4 is an illustration of a gyroscope in accordance with an example embodiment.

FIG. 4 is an illustration of a gyroscope 100 in accordance with an example embodiment. Gyroscope 100 is a tri-axial gyroscope where a first gyroscope is oriented to an X-axis, a second gyroscope is oriented to a Y-axis, and a third gyroscope is oriented to a Z-axis. Gyroscope 100 is a dynamic device that produces an output as the device is moved. Gyroscope 100 does not produce an output under static conditions. In one embodiment, gyroscope 100 is a solid state MEMS (Microelectromechanical System). A MEMS gyroscope has a small form factor suitable for placement within a prosthetic component. A MEMS gyroscope is formed by photolithographic processes on a silicon substrate. A single MEMS gyroscope of gyroscope 100 comprises a resonating mass that vibrates about its axis of symmetry. Movement of gyroscope 100 affects the resonating mass. A rotation about the axis results in a Coriolis force being generated that is sensed or detected. The force measurement conversion from mechanical to electrical is built into the device. In one embodiment, a gyroscope includes a capacitor sensing structure. As the resonating mass moves out of plane due to movement of the gyroscope a corresponding change is produced in the capacitor. Thus, the mechanical movement is converted to an electrical parameter. Electronic circuitry can be coupled to gyroscope 100 to monitor the capacitance output or convert the capacitance value to an analog signal or a digital signal.

In general, gyroscope 100 is coupled to a bone of the musculoskeletal system. In the example, gyroscope 100 is coupled to a proximal end of a tibia. Gyroscope 100 can be placed in an insert or a tibial prosthetic component to measure alignment relative to the mechanical axis of the leg. Angles related to alignment of the leg can be measured by moving the leg through a predetermined movement. In one embodiment, a first leg movement and a second leg movement are performed with the measurement data of gyroscope 100 being provided to a computer. The computer will have software that can calculate one or more angles using the measurement data. The angles can be provided to a surgeon in real-time in the operating room to verify a correct leg alignment or to indicate corrections required to put the leg in correct alignment during installation of a knee joint. Similarly, gyroscope 100 could be used in a permanent prosthetic component to measure leg alignment or leg position by providing the measurement data to a microprocessor or DSP based device such as a smartphone.

Gyroscope 100 measures angular velocity related to the three axes X, Y, and Z when coupled to the tibia as shown in FIG. 2. In one embodiment, the three axes have a predetermined alignment relative to the prosthetic component in which it is placed. In the example, the leg or knee joint is rotated less than 360 degrees and the movement is being performed by the surgeon at a relatively slow speed. Thus, gyroscope 100 can detect small changes corresponding to misalignment of the leg to a mechanical axis. Gyroscope 100 is not affected by linear acceleration or linear velocity and only measures angular velocity. Acceleration and velocity are linked and therefore angular velocity is altered by angular acceleration. In one embodiment, gyroscope 100 has a range +−2000 degrees/second and an output rate of 20-128 Hertz. In the disclosed application, the angular velocity being measured is much less than the measurement range of the gyroscope. Reducing the measurement range will typically improve the sensitivity of gyroscope 100 for the alignment measurement. In one embodiment, gyroscope 100 and ancillary electronic circuitry used to measurement alignment of the muscular skeletal is powered by a power source. The power source can be a battery, capacitor, inductor, or other energy storage device that can last for the entire installation of the prosthetic joint. In one embodiment, the trial-insert is a single use device and is disposed of after surgery. Gyroscope 100 can be operated at the lower end of the output rate to maximize battery life without impact to the accuracy of the measurements. In one embodiment, a digital interface is used with gyroscope 100 to support coupling with control logic, a microcontroller, ASIC, microprocessor, or digital signal processor.

It should be noted that accelerometers have been used to measure muscular-skeletal alignment and have been found to not work under all circumstances. For example, using an accelerometer under a static measurement it is not possible to determine a three dimensional orientation from a single gravity reference. Also, under dynamic conditions, it is not possible to separate acceleration due to gravity from an applied acceleration due to an external force. The above-mentioned issues when using an accelerometer for muscular-skeletal alignment can manifest in producing error when one axis is aligned with gravity or the inability to distinguish roll and yaw.

Figure 5:
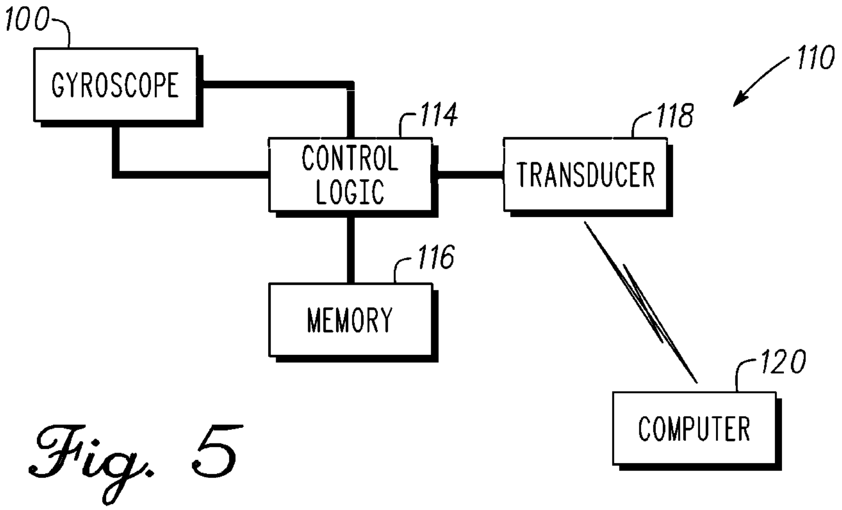
FIG. 5 is a block diagram of the gyroscope and electronic circuitry in accordance with an example embodiment.

FIG. 5 is a block diagram 110 of gyroscope 100 and electronic circuitry in accordance with an example embodiment. Gyroscope 100 is a MEMS tri-axial gyroscope as described in FIG. 4. The axes of gyroscope 100 are referenced to a prosthetic component or a bone surface to support an alignment measurement of the musculoskeletal system. In one embodiment, gyroscope 100 includes a digital interface that uses SPI or I2C communication protocols. Either interface can work at the low sample required for the alignment application. Electronic circuitry comprises control logic 114, memory 116, and transceiver 118. A computer 120 receives measurement data from gyroscope 100. In one embodiment, the electronic circuitry is housed in a prosthetic component.

Control logic 114 can comprise one or more of an FPGA, microcontroller, microprocessor, microprocessor, digital signal processor, or digital logic. In general, control logic 114 is configured to control a measurement process or measurement sequence to generate quantitative measurement data that supports calculation of muscular-skeletal alignment using gyroscope 100. Control logic 114 is operatively coupled to gyroscope 100. Control logic 114 includes one or more control signals that support the measurement process. Memory 116 is coupled to control logic 114. Memory 116 can include a software program to generate measurement data related to alignment of the muscular-skeletal system. The software program can be executed by control logic 114. Control logic 114 further includes input/output circuitry coupled to gyroscope 100 configured to receive measurement data. Control logic 114 can store the measurement data in memory 116. Transceiver 118 is coupled to input/output circuitry of control logic 114. Transceiver 118 is used to receive or transmit information or data.

Computer 120 is coupled to the electronic circuitry. Computer 120 can be coupled via a wired or wireless coupling. In one embodiment, computer 120 is placed outside a sterile field of an operating room. A display of computer 120 is placed in view of a surgical team for receiving muscular-skeletal alignment information. Computer 120 receives measurement data from the electronic circuitry and gyroscope 100. Computer 120 can also transmit information to the electronic circuitry that initiates or supports the measurement process. Computer 120 can include software to process the measurement data from gyroscope 100, perform calculations, calculate alignment, provide a workflow, and display information. For example, computer 120 can provide a visual image of a femur and tibia misaligned to the mechanical axis. Computer 120 could also produce one or more different workflows to correct the misalignment based on the quantitative measurement data.

Figure 6:
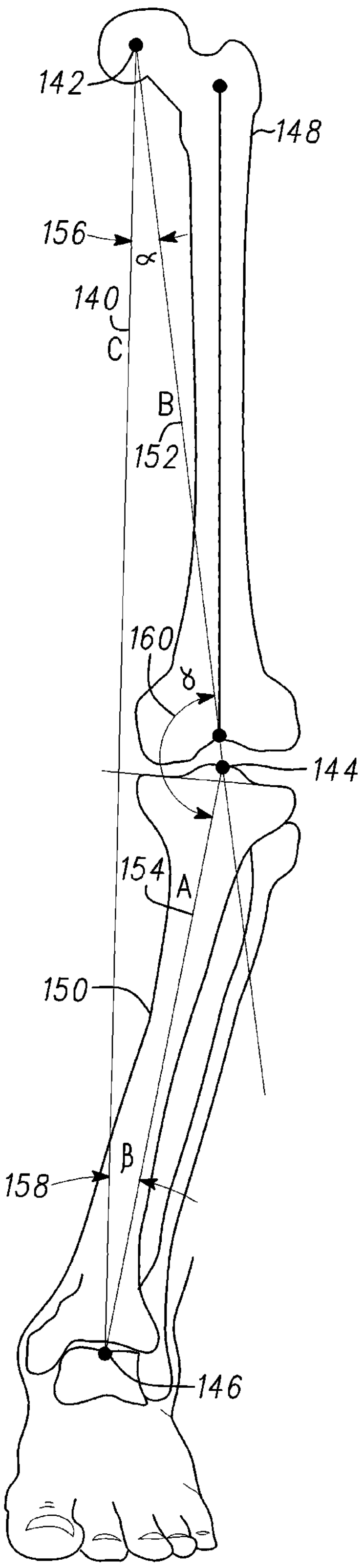
FIG. 6 is an illustration of angles measured by a gyroscope coupled to a proximal end of a tibia in accordance with an example embodiment.

FIG. 6 is an illustration of angles measured by a gyroscope coupled to a proximal end of a tibia 150 in accordance with an example embodiment. In general, a surgeon prepares bone surfaces to receive a prosthetic component. The bone cuts on the prepared surface of a bone can affect how the bone geometrically interacts with another bone or prosthetic component. In the example, a total knee arthroplasty (TKA) replaces a faulty knee joint with a prosthetic knee joint. The alignment of the prosthetic knee components to one another and to the femur and tibia affects leg performance and reliability. Misalignment affects leg kinematics, joint wear, or could lead to a catastrophic issue requiring joint replacement. Thus, accurate quantitative measurement of the alignment prior to installation, during installation, or post installation of the prosthetic components will improve both short-term and long term results of the patient. Furthermore, the quantitative measurement data can be used by manufacturers of prosthetic components to assess and improve the designs.

Figure 14:
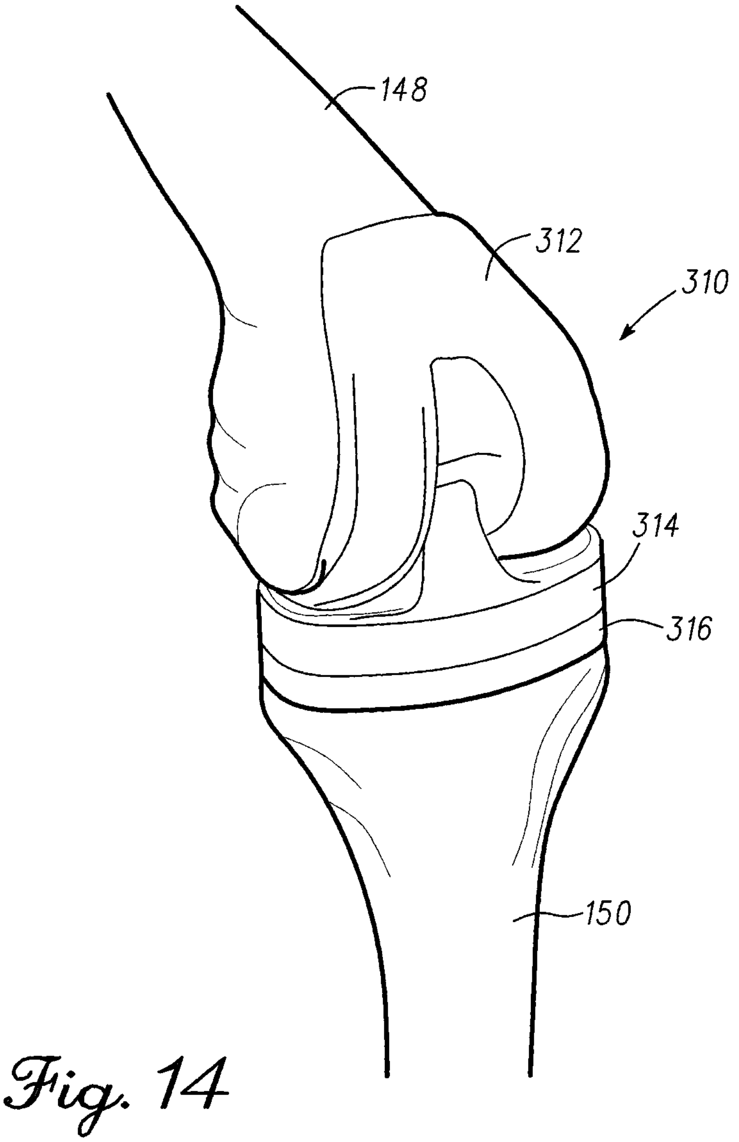
FIG. 14 is an illustration of a prosthetic knee joint including the tri-axial gyroscope in accordance with an example embodiment.

Referring to FIG. 14, a knee joint 310 comprises a femoral prosthetic component 312, an insert 314, and a tibial prosthetic component 316. Femoral prosthetic component 312 is coupled to prepared bone surfaces on a distal end of a femur 148. Tibial prosthetic component 316 is coupled to a prepared bone surface on a proximal end of a tibia 150. Insert 314 couples to tibial prosthetic component 316 and includes articular surfaces to support movement of the leg. A tri-axial gyroscope is part of a measurement system that provides quantitative measurement data related to alignment in real-time. In the example, the tri-axial gyroscope is in insert 314. The gyroscope is in a predetermined orientation within insert 314. The measurement data output by the tri-axial gyroscope is used in conjunction with the leg geometry to calculate angles that can be used to verify that the leg is in alignment.

Referring back to FIG. 6, geometrically a triangle can be formed around the leg that relate to the alignment of the leg. A line 140 represents a line drawn from a center 142 of a femoral head to a center 146 of an ankle and is indicated by the letter C. A line 152 is drawn from center 142 of the femoral head to a center 144 of a knee joint. Line 152 is also identified by a letter B. A line 154 is drawn from center 144 of the knee joint to center 146 of the ankle. Line 154 is also identified by a letter A and corresponds to tibia 150. The triangle comprises lines 140, 152, and 154. In one embodiment, the center of the knee joint can be related to a bone landmark such as the medial tibial spine. The triangle comprises three angles that can be measured using measurement data from a tri-axial gyroscope coupled to tibia 150 in conjunction with the lengths of line 140, line 152, and line 154.

Angles related to the frontal plane of a total knee arthroplasty can be calculated using measurement data from a tri-axial gyroscope coupled to tibia 150 similar to that disclosed in FIG. 2 or within a prosthetic component as disclosed in FIG. 3. An angle 156 that is identified by a letter α corresponds to a hip angle. The hip angle is an angle formed by line 140 and line 152 having an intersection at center 142 of the femoral head. An angle 160 that is identified by a letter $\gamma$ is a knee angle. The knee angle is an angle formed by line 152 and line 154 having an intersection at the center of the knee joint. An angle 158 is identified by a letter B is an ankle angle. The ankle angle is an angle formed by line 140 and line 154 having an intersection at the center of the ankle. In particular, the knee angle or angle 160 in the sagittal and frontal planes is used to support alignment of the prosthetic components. In one embodiment, the length of line B is known. Similarly, the length of line A is known. Measurement of A and B is disclosed herein below. The measurement of line 152 corresponding to femur 148 and line 154 corresponding to tibia 150 will be provided in more detail herein below. The Law of Cosines equation is used to solve for the length of line 140 corresponding to the distance from the center 142 of the femoral head of femur 148 to the center 146 of the ankle. The Law of Cosines is represented in equation 1 listed below.

$$A^2 = B^2 + C^2 - 2BC\cos(\alpha_{Frontal}) \quad \text{Equation 1}$$

Figure 7:
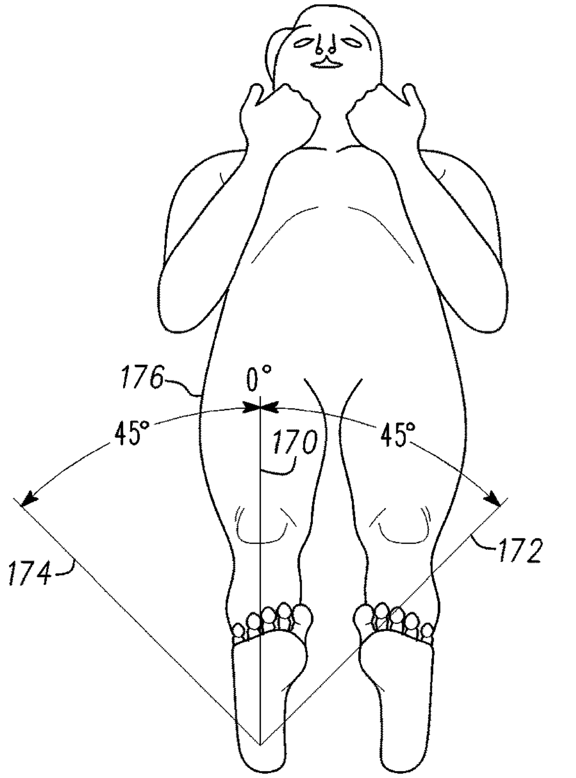
FIG. 7 is an illustration of a first movement of a leg in accordance with an example embodiment.

A measurement system using a tri-axial gyroscope is coupled to tibia 150. In the example, tri-axial gyroscope 62 of FIG. 2 has the axes aligned as indicated to tibia 44 of FIG. 2. The angle $\alpha_{Frontal}$ can be measured by moving the leg through a first movement using measurement data from the tri-axial gyroscope 62. The angle $\alpha_{Frontal}$ IS a frontal hip angle that is measured from measurement data generated by the tri-axial gyroscope during the first movement. In general, the first movement is a rotation of the leg that may produce angular velocities on each axis. Referring to FIG. 7, the first movement is illustrated in accordance with an example embodiment. In the example, the right leg 176 is used to show the first movement. The motion can be performed on either leg in a similar manner. Leg 176 is placed in full extension. In one embodiment, the Z-axis of the tri-axial gyroscope aligns to the joint line or line 170. The entire leg is rotated about the Z-axis or joint line of the leg with the leg in full extension. In the first movement, the foot, lower leg, and the upper leg are rotated together. A neutral position corresponding to 0 degrees is indicated by line 170 with the patient lying on his or her back with the foot extending upwards with no torque on the knee or ankle joint. The first movement comprises rotating the entire leg 176 internally towards line 172 and externally towards line 174. In one embodiment, leg 176 is rotated 45 degrees on either side of the neutral position. The total movement of 90 degrees has been found sufficient to provide accurate measurement data from the tri-axial gyroscope on each axis. The total movement can be more or less than 90 degrees. It was found that the rate at which leg 176 is rotated affects the accuracy of the measurement more than the amount of total rotation. In one embodiment, leg 176 is rotated between lines 172 and 174 at a rate 1.5 radians/second to 8.0 radians/second. The first movement rotation can be further specified as a slow rotation and a fast rotation where the rotation is performed within a predetermined rate range. In one embodiment, a slow rotation of leg 176 comprises a rate of 1.5-2.0 radians a second that corresponds to approximately 86-115 degrees/second. A fast rotation of leg 176 comprises a rate of 6.0-8.0 radians/second that corresponds to approximately 344-458 degrees/second.

Maintaining movement of leg 176 within these ranges assures the tri-axial MEMs gyroscope will produce accurate angle measurements related to alignment of the musculoskeletal system. The equations herein represent the embodiment where the Z-axis of the tri-axial gyroscope aligns with the mechanical axis of the femur corresponding to line 152 of FIG. 6.

Referring back to FIG. 6 the first movement produces quantitative measurement data from the tri-axial gyroscope. In one embodiment, the tri-axial gyroscope measurement data is sent to a computer for calculating one or more parameters. In the example where tri-axial gyroscope is placed in a prosthetic component, the measurement data is wirelessly transmitted to the computer. A sagittal plane knee angle (posterior/anterior slope) is calculated by the computer using the tri-axial gyroscope measurement data related to the X-axis and Z-axis via direct calculation. A frontal plane angle (*varus*/valgus) is calculated by the computer using the tri-axial gyroscope measurement data related to the Y-axis and Z-axis via the Law of Cosines. The computer directly plots the appropriate gyroscope axes as disclosed above with respect to one another. In other words, the gyroscope X-axis is plotted versus the Z-axis (sagittal plane) and the computer calculates a line fitted to the measurement data. Similarly, the gyroscope Y-axis is plotted versus the Z-axis (frontal plane) and the computer calculates a line fitted to the measurement data. The X-axis versus Z-axis calculated line is used to directly calculate the sagittal knee angle via Equation 2. The Y-axis versus Z-axis calculated line is used in conjunction with Equation 3 to calculate the frontal hip angle. The sagittal knee and frontal hip angles are calculated in the computer using Equations 2 and 3, respectively.

$$\gamma_{Sagittal} = \arctan(\Delta\omega_X/\Delta\omega_Z) \quad \text{Equation 2}$$

$$\alpha_{Frontal} = \arctan(\Delta\omega_Y/\Delta\omega_Z) \quad \text{Equation 3}$$

The angle $\alpha_{Frontal}$ corresponds to the hip angle formed by line 140 and line 152 within the triangle formed by the leg. The angle $\alpha_{Frontal}$ is then used in the Law of Cosines to solve for line 140 that is also identified as C on FIG. 6. The length of the joint line or line 140 is solved for in Equation 4 and listed below.

$$C = \left(2Bcos(\alpha_{Frontal}) + (2)^{1/2}\left(2A^2 - B^2 + B^2\cos(2\alpha_{Frontal})\right)^{1/2}\right)/2 \quad \text{Equation 4}$$

The computer having calculated the length of frontal joint line length or line 140 length uses the calculated length of line 140 to generate a frontal knee angle. The frontal knee angle corresponds to angle $\gamma_{Frontal}$ that is the knee angle formed by line 152 and line 154 within the triangle formed by the leg. The frontal knee angle is calculated by the computer using Equation 5 listed below.

$$\gamma_{Frontal} = \arccos\left((A^2 + B^2 - C^2)/2AB\right) \quad \text{Equation 5}$$

Figure 8:
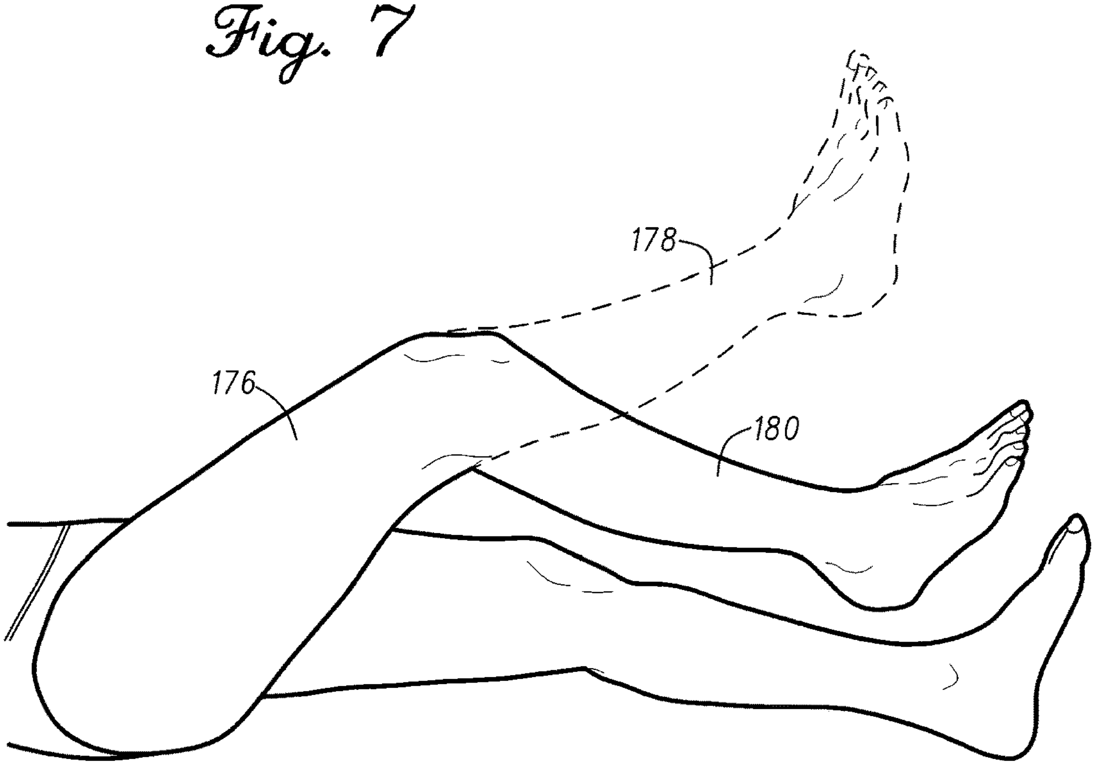
FIG. 8 is an illustration of a second movement of the leg in accordance with an example embodiment.

Referring to FIG. 8, a second movement is illustrated in accordance with an example embodiment. In the example, the right leg 176 is used to show the second movement. The motion can be performed on either leg in a similar manner. The femur of leg 176 is elevated from horizontal. Leg 176 can lifted by someone in the surgical team or supported by a fixture to a stable position. The second movement is a rotation of the tibia about the femur or a kicking motion. Elevating the femur allows the tibia to move freely from flexion 180 to extension 178. In one embodiment, leg 176 is rotated between flexion 180 and extension 178 at a rate 1.5 radians/second to 4.0 radians/second. The second movement rotation can be further specified as a slow rotation and a fast rotation where the rotation is performed within a predetermined rate range. In one embodiment, a slow rotation of leg 176 in the second movement comprises a rate of 1.5-2.0 radians a second that corresponds to approximately 86-115 degrees/second. A fast rotation of leg 176 in the second movement comprises a rate of approximately 4.0 radians/second that corresponds to approximately 229 degrees/second.

Referring back to FIG. 6 the second movement produces quantitative measurement data from the tri-axial gyroscope. In one embodiment, the tri-axial gyroscope measurement data is sent to a computer for calculating one or more parameters. In the example where the tri-axial gyroscope is placed in a prosthetic component, the measurement data from the second movement is wirelessly transmitted to the computer. A direct calculation of an angle is possible by comparing the appropriate axes. For example, there is no triangle formed to use the Law of Cosines when looking at the transverse plane of the tibial tray through the second rotation. The computer can plot the X-axis against the Y-axis and fit a line to that the measurement data from the tri-axial gyroscope corresponding to the second movement of the leg. The calculated line from the X-axis against the Y-axis is used in Equation 6 to calculate the knee transverse angle. The angle is calculated using equation 6 in the computer and calculating the arc tangent of 1 divided by the slope of the line related to the knee tibial transverse angle or the slope of the line related to the knee tibial frontal angle.

$$Y_{Transverse} = \arctan(\Delta\omega_X / \Delta\omega_Y) \qquad \text{Equation 6}$$

Figure 9:
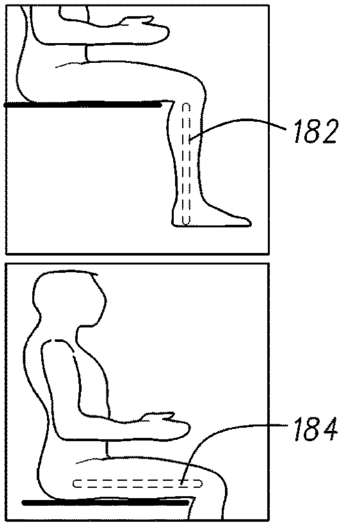
FIG. 9 is an illustration of the required lower extremity measurements from a patient in a sitting position in accordance with an example embodiment.

FIG. 9 is an illustration of a patient in a sitting position in accordance with an example embodiment. As disclosed herein above the length of a femur and a length of a tibia are needed to calculate alignment of the leg. As mentioned previously, images of the femur or tibia can be measured and scaled to determine length of each bone. In particular, a center of a femoral head and the center of the knee can be identified in an image. Similarly, the center of the knee to the center of the ankle can be identified in an image. In one embodiment, the images can be scanned into the computer or digital images can be provided to the computer. The computer can then identify bone landmarks related to measuring the length of a bone of the musculoskeletal system, measure the length of a bone image, and scale the bone image to provide a length for the bone.

Alternatively, a measurement of each bone can be made prior to a surgery. The measurement can be made using a measuring device such as a tape measure or ruler. In the example, a femur 184 and a tibia 182 are measured. Although the measurements cannot be exact, it has been found that the measurements as described herein below do not impact the calculations significantly and support alignment measurement of the musculoskeletal system within a tolerance that provides effective installation of prosthetic components. The patient is placed on a chair or table in a sitting position. An approximate length of tibia 182 can be measured from the bottom of the foot to a lateral condyle of tibia 182. The lateral condyle can be identified by moving the leg or tibia 182 in flexion as the patient is in the sitting position and tracing the condyles of the femur with the fingers to tibia 182. On the lateral side of the knee the femoral condyle will contact the lateral condyle of tibia 182 or articular surface of the tibia 182. A ruler can be placed adjacent to the leg to measure from the bottom of the foot to the lateral condyle.

Similarly, the length of femur 184 can be measured. In one embodiment, an approximate length of the femur can be measured from the greater trochanter at a proximal end of the femur to the femoral epicondyle. The greater trochanter can be found by tracing the pelvic region of the leg to femur 184 until a bony protrusion (e.g. greater trochanter) is identified. The patient can move the leg in a manner that moves femur 184 to verify corresponding movement of the greater trochanter. The femoral epicondyle can be found in a similar manner. The femoral lateral epicondyle is a bony projection near the distal end of femur 184 where ligaments or tendons are attached. The femoral lateral epicondyle can be detected through feel of the bony projection. A ruler can be placed adjacent the leg to measure from the greater trochanter to the femoral lateral epicondyle to approximately measure the length of femur 184.

Figure 10:
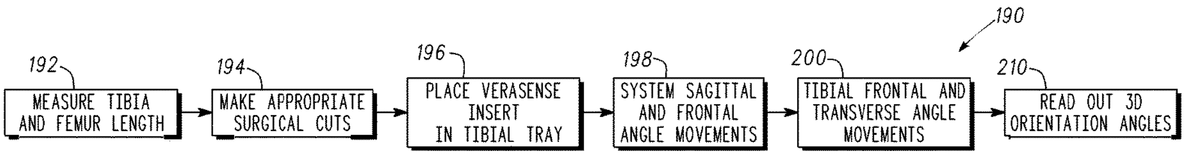
FIG. 10 is an illustration of a clinical flow to measure alignment of a leg in accordance with an example embodiment.

FIG. 10 is an illustration of a clinical flow to measure alignment of a leg in accordance with an example embodiment. A method of alignment using a measurement system is disclosed. The method can be practiced with more or less steps and is not limited to the order of steps shown. The method is not limited to the knee example but can be used for hip, knee, shoulder, ankle, elbow, spine, hand, wrist, foot, bone, and musculoskeletal system. The components listed in the method can be referred to and are disclosed in FIGS. 2 and 3.

In a step 192, a length of a tibia and a femur are measured. As disclosed herein above, the tibia and the femur can be measured prior to surgery to install a prosthetic knee joint. The tibia and the femur can be measured using a ruler or other measurement device by locating and identifying bone landmarks of the tibia or the femur and measuring the distance between the bone landmarks. A length of a tibia can be approximated by measuring from a bottom of a foot to a lateral condyle. A length of a femur can be approximated by measuring from a greater trochanter to a femoral epicondyle. Alternatively, images of the tibia and the femur can be provided to a computer. The computer can identify bone features and landmarks, measure the length of the bone, and scale the measurement to a bone length.

The alignment system comprises three gyroscopes, electronic circuitry, and a computer. The three gyroscopes can also be housed in a single package as a tri-axial gyroscope. In one embodiment, the gyroscope and electronic circuitry are housed in a trialing prosthetic component. The trialing prosthetic component can further include one or more sensors for measuring a parameter of the muscular-skeletal system and a power source. The trialing prosthetic component can be single use device and is disposed of after being used in the operating room. Measurement data from the gyroscope can be wirelessly transmitted to the computer. The computer can perform calculations and execute software to measure alignment in real-time and provide alignment information and data in the operating room. The alignment system can be used in a similar fashion to provide measurement data to a computer if the gyroscope is placed in a permanent prosthetic component to monitor alignment long-term. In the example where the tibia and femur are measured, the length of the tibia and the length of the femur are entered into to the computer.

In a step 194, surgical cuts or bone cuts are made to the tibia to receive a tibial prosthetic component. In one embodiment, the gyroscope couples to a prepared bone of the proximal end of the tibia of a leg. The tibial prosthetic component comprises a tibial tray and a keel. The keel of the tibial prosthetic component is inserted into the tibial medullary canal to support, stabilize, and position the tibial prosthetic component to the prepared bone surface. Installing the tibial prosthetic component to the proximal end of the tibia couples a bottom surface of the tibial tray to the prepared bone surface. In one embodiment, the tibial prosthetic component is aligned to or relative to a bone landmark of the tibia. The tibial prosthetic component is typically glued to the tibia.

In a step 196, an insert is placed in the tibial tray of the tibial prosthetic component. In one embodiment, a tri-axial gyroscope and the electronic circuitry are housed in a prosthetic component. In the example, the tri-axial gyroscope, electronic circuitry, and power source are housed in an insert. One plane of the tri-axial gyroscope can be parallel to a prepared bone surface of the proximal end of the tibia, a surface of the tibial tray, or a bottom surface of the insert. A first axis of the tri-axial gyroscope can be aligned to the anterio-posterio direction of the insert. A second axis of the tri-axial gyroscope can be aligned to the medial-lateral direction of the insert. A third axis of the tri-axial gyroscope can be perpendicular to the plane of the first and second axes. Thus, the tri-axial gyroscope can have a predetermined alignment with the insert, the tibial prosthetic component, and the tibia that relates to the anatomy of the leg and the alignment of the leg.

In a step 198, a first movement is performed. The gyroscope responds to movement and provides angular velocities related to each axis. In one embodiment, the gyroscope measurement data related to the first movement is used to measure a system sagittal angle and a system frontal angle. The leg is placed in extension for the first movement. The leg is then rotated about the hip and an ankle. The electronic circuitry of the insert transmits angular velocity measurement data related to each axis from the tri-axial gyroscope as the leg moves through the first movement. The first movement can be repeated one or more times. In one embodiment, the leg is rotated 45 degrees on either side of a neutral or zero degree position. Furthermore, the leg has to be rotated above a predetermined rate. A slow rotation of the leg comprises a rate of 1.5-2.0 radians a second that corresponds to approximately 86-115 degrees/second. A fast rotation of the leg comprises a rate of 6.0-8.0 radians/second that corresponds to approximately 344-458 degrees/second. The measurement data is sent to and received by a computer. The computer includes a software program that uses the measurement data from the gyroscope to calculate alignment. The computer calculates a system sagittal angle and a system frontal angle related to leg alignment from the measurement data related to the first movement of the leg. Other calculations that are performed by the computer are disclosed in detail in FIG. 6 herein above.

In a step 200, a second movement is performed. The gyroscope responds to movement and provides angular velocities related to each axis. In one embodiment, the gyroscope measurement data related to the second movement is used to measure a tibial frontal angle and a tibial transverse angle. In the second movement the patient is in a supine position with the femur elevated. The second movement comprises rotating the tibia about a femur. This movement is similar to a kicking motion where the femur is stationary in the elevated position and the tibia moves from flexion to extension. The electronic circuitry of the insert transmits angular velocity measurement data related to each axis from the gyroscope as the leg moves through the second movement. The second movement can be repeated one or more times. The rotation of the tibia about the femur has to be rotated above a predetermined rate. A slow rotation of the leg in the second movement comprises a rate of 1.5-2.0 radians a second that corresponds to approximately 86-115 degrees/second. A fast rotation of the leg in the second movement comprises a rate of approximately 4.0 radians/second that corresponds to approximately 229 degrees/second. The measurement data is sent to and received by a computer. The computer includes a software program that uses the measurement data from the gyroscope to calculate alignment. The computer calculates the tibial frontal angle and the tibial transverse angle related to leg alignment from the measurement data related to the second movement of the leg. Other calculations that are performed by the computer are disclosed in detail in FIG. 6 herein above.

In a step 202, a read out 3D orientation angles are provided in real-time. In one embodiment, the computer is coupled to a display that can be viewed by a surgical team in the operating room. Measurement data from the three gyroscopes or a tri-axial gyroscope has been provided to the computer as the leg undergoes at least two different movements. One or more metrics are provided on the display to the surgical team related to the alignment of the leg after the first movement or the second movement is completed. The system sagittal angle, the system frontal angle, the tibial frontal angle or a tibial transverse angle can be displayed on the display. In one embodiment, the 3D orientation angles are the system sagittal angle for the sagittal plane, the system frontal angle minus the tibial frontal angle for the frontal plane, and the tibial transverse angle for the transverse plane. The computer could also generate other measurement data related to alignment from the data collected from the gyroscopes and other sensors. The computer can also provide visual, audible, or haptic feedback to support the quantitative measurement data. For example, a femur, prosthetic knee joint, and tibia can be displayed on the screen in a manner that illustrates the measured angles. The computer can simulate movement of the leg and provide alignment information over a range of motion. The computer can also provide one or more workflows that can be implemented to bring the leg into better alignment using the measurement data. The workflows would comprise steps to alter the alignment such as bone cuts, ligament tensioning, or shimming.

Figure 11:
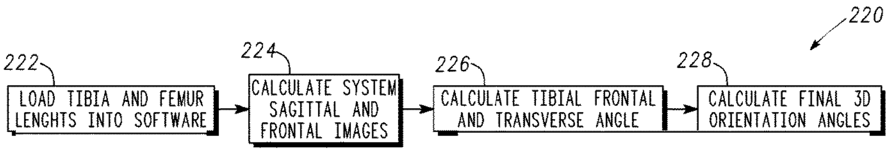
FIG. 11 is an illustration of a software flow to measure alignment of a leg in accordance with an example embodiment.

FIG. 11 is an illustration of a software flow 220 to measure alignment of a leg in accordance with an example embodiment. A method of alignment using a measurement system is disclosed. The method can be practiced with more or less steps and is not limited to the order of steps shown. The method is not limited to the knee example but can be used for hip, knee, shoulder, ankle, elbow, spine, hand, wrist, foot, bone, and musculoskeletal system. The components listed in the method can be referred to and are disclosed in FIGS. 2 and 3.

A trial measurement system comprises a prosthetic component and a computer. In one embodiment, the trial measurement system can measure leg alignment. The prosthetic component includes a tri-axial gyroscope, electronic circuitry, and a power source. The electronic circuitry couples to the tri-axial gyroscope, controls a measurement process, and transmits measurement data from the tri-axial gyroscope. The prosthetic component has an internal cavity that houses the tri-axial gyroscope, electronic circuitry, and the power source. The internal cavity is hermetically sealed from an external environment. The tri-axial gyroscope is aligned respectively to an anterio-posterio axis and a medial-lateral axis of the prosthetic component. A third axis of the tri-axial gyroscope can be aligned to the joint line when the leg is in extension. In one embodiment, the prosthetic component can be an insert or a tibial prosthetic component. The measurement process is initiated when a leg undergoes at least one movement that supports an alignment measurement of the leg. The computer is configured to receive measurement data from the tri-axial gyroscope. In one embodiment, the prosthetic component sends the measurement data wirelessly and encrypted. The computer is in proximity to the prosthetic component to provide alignment metrics in real-time. The computer is configured to calculate at least one of a system sagittal angle, a system frontal angle, a tibial frontal angle, or a tibial transverse angle from the measurement data.

In a step 222, a tibia and a femur length is loaded into a computer. The trial measurement system is configured to store the length of the tibia and the length of the femur in memory on the computer. The computer includes a software program that uses the tibia and the femur length in at least one calculation. In a step 224, a tri-axial gyroscope in an insert provides angular velocities related to a first movement of a leg. The tri-axial gyroscope is configured having a predetermined orientation in relation to a tibia of the leg. In one embodiment, the leg is placed in extension for the first movement. The leg is then rotated about the hip and an ankle. In one embodiment, the tri-axial gyroscope is configured to measure the leg rotated about the hip and the ankle at greater than 1.5 radians/second but less than 8.0 radians/second. The dynamic measurement data generated by the gyroscope is transmitted to the computer. The software program is executed calculating the system sagittal angle and system frontal angle. The system sagittal angle and the system frontal angle can be displayed on a display coupled to the computer.

In a step 226, the tri-axial gyroscope in the insert provides angular velocities of related to a second movement of a leg. In one embodiment, the leg is placed in extension for the first movement. In the second movement the patient is in a supine position with the femur elevated. The second movement comprises rotating the tibia about a femur. In one embodiment, the tri-axial gyroscope is configure to measure the tibia rotated about the femur at greater than 1.5 radians/second but less than 4.0 radians/second. The dynamic measurement data generated by the tri-axial gyroscope is transmitted to the computer. The software program is executed calculating the tibial frontal angle and the tibial transverse angle. The tibial frontal angle and the tibial transverse angle can be displayed on a display coupled to the computer. Examples of the equations used in steps 224 and 226 by the computer are disclosed in FIG. 6 herein above.

In a step 228, final 3D orientation angles are calculated. In one embodiment, the angles are provided in real-time. Measurement data from the three gyroscopes or a tri-axial gyroscope is transmitted to the computer as the leg undergoes at least a first leg movement and a second leg movement. One or more metrics are provided on the display to the surgical team related to the alignment of the leg after the first movement or the second movement is completed. A software program is executed and the 3D orientation angles are calculated by the computer using quantitative measurement data from the gyroscopes. In one embodiment, the system sagittal angle for the sagittal plane, the system frontal angle minus the tibial frontal angle for the frontal plane, and the tibial transverse angle for the transverse plane comprise the 3D orientation angles that are displayed on a display of the computer. The computer could also generate other measurement data related to alignment from the data collected from the gyroscopes and other sensors. The computer can also provide visual, audible, or haptic feedback to support the quantitative measurement data or calculations. For example a software program can provide visual feedback related to the 3D orientation angles by illustrating a femur, prosthetic components, and tibia coupled together with the measured angles. The computer can simulate movement of the leg and provide alignment information over a range of motion. Visual, audible, or haptic feedback can be used to indicate where alignment is outside a predetermined range. The computer can also provide one or more workflows that can be implemented to bring the leg into better alignment using the measurement data. The workflows would comprise steps to alter the alignment such as bone cuts, ligament tensioning, or shimming.

Figure 12:
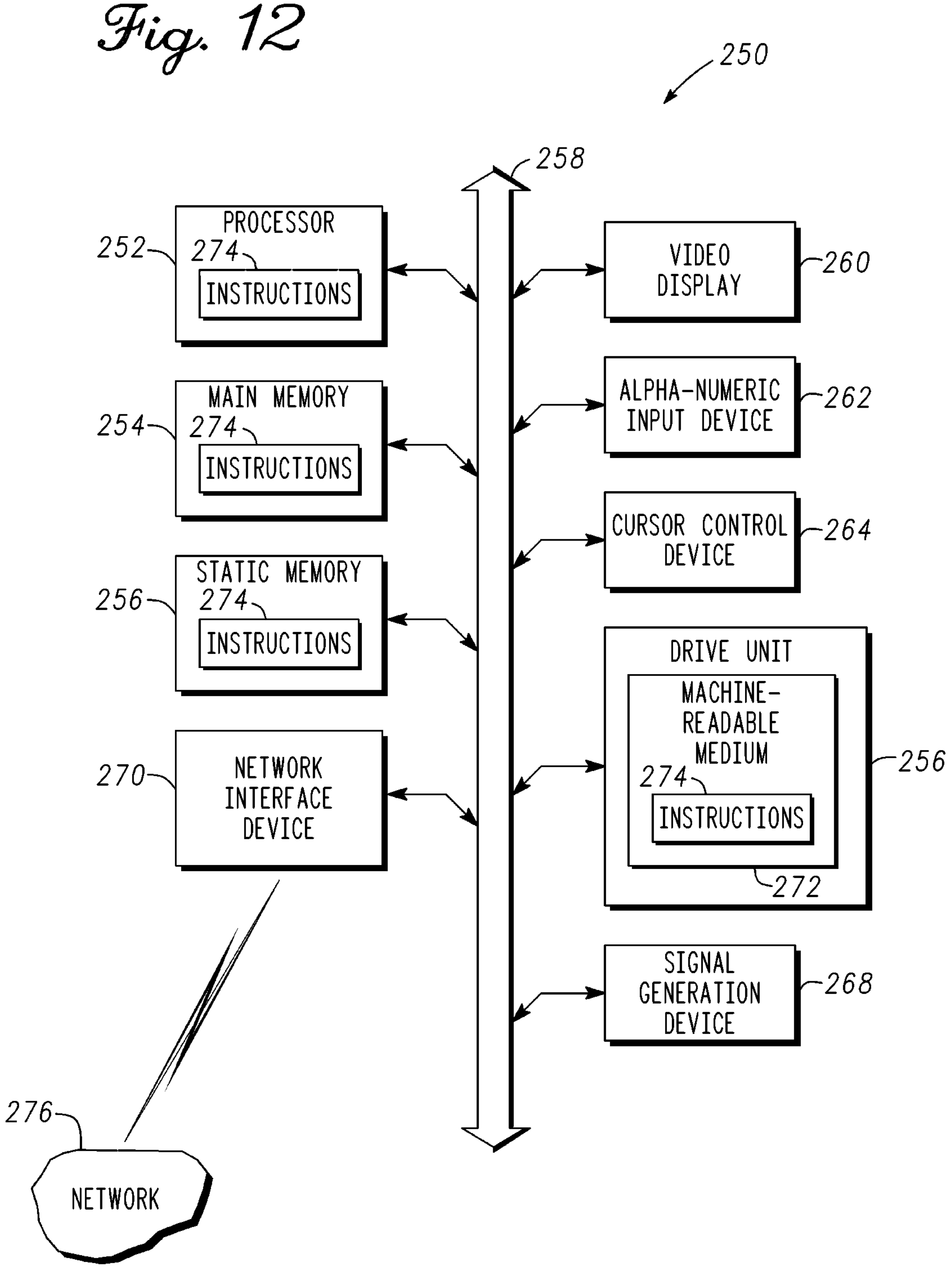
FIG. 12 is a block diagram of a measurement system or computer in accordance with an example embodiment.

FIG. 12 is a block diagram of a measurement system or computer in accordance with an example embodiment. The exemplary diagrammatic representation of a machine, system, or computer in the form of a system 250 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, logic circuitry, a sensor system, an ASIC, an integrated circuit, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

System 250 may include a processor 252 (e.g., a central processing unit (CPU), a graphics processing unit (GPU, or both), a main memory 254 and a static memory 256, which communicate with each other via a bus 258. System 250 may further include a video display unit 260 (e.g., a liquid crystal display (LCD), a flat panel, a solid state display, or a cathode ray tube (CRT)). System 250 may include an input device 262 (e.g., a keyboard), a cursor control device 262 (e.g., a mouse), a disk drive unit 266, a signal generation device 268 (e.g., a speaker or remote control) and a network interface device 270.

The disk drive unit 266 can be other types of memory such as flash memory and may include a machine-readable medium 272 on which is stored one or more sets of instructions 274 (e.g., software) embodying any one or more of the methodologies or functions described herein, including those methods illustrated above. Instructions 274 may also reside, completely or at least partially, within the main memory 254, the static memory 256, and/or within the processor 252 during execution thereof by the system 250. Main memory 254 and the processor 252 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 274, or that which receives and executes instructions 274 from a propagated signal so that a device connected to a network environment 276 can send or receive voice, video or data, and to communicate over the network 276 using the instructions 274. The instructions 274 may further be transmitted or received over a network 276 via the network interface device 270.

While the machine-readable medium 272 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

Figure 13:
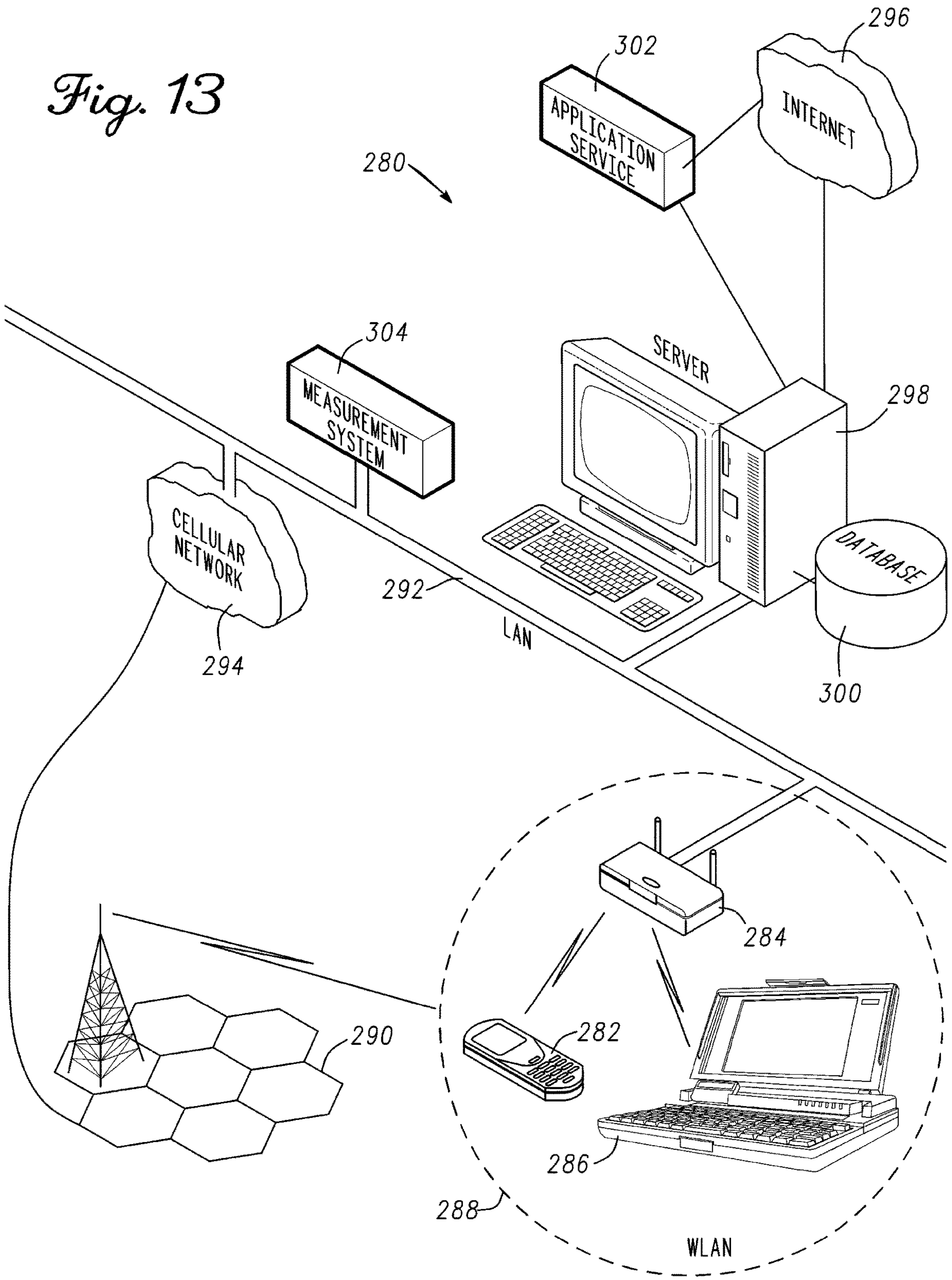
FIG. 13 is an illustration of a communication network for measurement and reporting in accordance with an exemplary embodiment.

FIG. 13 is an illustration of a communication network 280 for measurement and reporting in accordance with an exemplary embodiment. Briefly, the communication network 280 expands broad data connectivity to other devices or services. As illustrated, the measurement and reporting system 304 can be communicatively coupled to the communications network 280 and any associated systems or services.

As one example, measurement system 304 can share its parameters of interest (e.g., angles, load, balance, distance, alignment, displacement, movement, rotation, and acceleration) with remote services or providers, for instance, to analyze or report on surgical status or outcome. This data can be shared for example with a service provider to monitor progress or with plan administrators for surgical monitoring purposes or efficacy studies. The communication network 280 can further be tied to an Electronic Medical Records (EMR) system to implement health information technology practices. In other embodiments, the communication network 280 can be communicatively coupled to HIS Hospital Information System, HIT Hospital Information Technology and HIM Hospital Information Management, EHR Electronic Health Record, CPOE Computerized Physician Order Entry, and CDSS Computerized Decision Support Systems. This provides the ability of different information technology systems and software applications to communicate, to exchange data accurately, effectively, and consistently, and to use the exchanged data.

The communications network 280 can provide wired or wireless connectivity over a Local Area Network (LAN) 292, a Wireless Local Area Network (WLAN) 288, a Cellular Network 294, and/or other radio frequency (RF) system (see FIG. 4). The LAN 292 and WLAN 288 can be communicatively coupled to the Internet 296, for example, through a central office. The central office can house common network switching equipment for distributing telecommunication services. Telecommunication services can include traditional POTS (Plain Old Telephone Service) and broadband services such as cable, HDTV, DSL, VoIP (Voice over Internet Protocol), IPTV (Internet Protocol Television), Internet services, and so on.

The communication network 280 can utilize common computing and communications technologies to support circuit-switched and/or packet-switched communications. Each of the standards for Internet 296 and other packet switched network transmission (e.g., TCP/IP, UDP/IP, HTML, HTTP, RTP, MMS, SMS) represent examples of the state of the art. Such standards are periodically superseded by faster or more efficient equivalents having essentially the same functions. Accordingly, replacement standards and protocols having the same functions are considered equivalent.

The cellular network 294 can support voice and data services over a number of access technologies such as GSM-GPRS, EDGE, CDMA, UMTS, WiMAX, 2G, 3G, WAP, software defined radio (SDR), and other known technologies. The cellular network 294 can be coupled to base receiver 290 under a frequency-reuse plan for communicating with mobile devices 282.

The base receiver 290, in turn, can connect the mobile device 282 to the Internet 296 over a packet switched link. The internet 296 can support application services and service layers for distributing data from the measurement system 304 to the mobile device 282. Mobile device 282 can also connect to other communication devices through the Internet 296 using a wireless communication channel.

The mobile device 282 can also connect to the Internet 296 over the WLAN 288. Wireless Local Access Networks (WLANs) provide wireless access within a local geographical area. WLANs are typically composed of a cluster of Access Points (APs) 284 also known as base stations. The measurement system 304 can communicate with other WLAN stations such as laptop 286 within the base station area. In typical WLAN implementations, the physical layer uses a variety of technologies such as 802.11b or 802.11g WLAN technologies. The physical layer may use infrared, frequency hopping spread spectrum in the 2.4 GHz Band, direct sequence spread spectrum in the 2.4 GHz Band, or other access technologies, for example, in the 5.8 GHZ ISM band or higher ISM bands (e.g., 24 GHZ, etcetera).

By way of the communication network 280, the measurement system 304 can establish connections with a remote server 298 on the network and with other mobile devices for exchanging data. The remote server 298 can have access to a database 300 that is stored locally or remotely and which can contain application specific data. The remote server 298 can also host application services directly, or over the Internet 296.

It should be noted that very little data exists on implanted orthopedic devices. Most of the data is empirically obtained by analyzing orthopedic devices that have been used in a human subject or simulated use. Wear patterns, material issues, and failure mechanisms are studied. Although, information can be garnered through this type of study it does yield substantive data about the initial installation, post-operative use, and long term use from a measurement perspective. Just as each person is different, each device installation is different having variations in initial loading, balance, and alignment. Having measured data and using the data to install an orthopedic device will greatly increase the consistency of the implant procedure thereby reducing rework and maximizing the life of the device. In at least one exemplary embodiment, the measured data can be collected to a database where it can be stored and analyzed. For example, once a relevant sample of the measured data is collected, it can be used to define optimal initial measured settings, geometries, and alignments for maximizing the life and usability of an implanted orthopedic device.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

What is claimed is:

1. A method of measuring leg alignment, comprising:
moving a leg through at least one first movement;
generating measurement data corresponding to the at least one first movement via a measurement system including a tibial stem inserted into a tibia of the leg;
using the measurement data corresponding to the at least one first movement, determining a first angle included in a triangle formed by a first line extending from a hip joint of the leg to a knee joint of the leg, a second line extending from the knee joint to an ankle joint of the leg, and a third line extending from the hip joint to the ankle joint, wherein a first length of the first line and a second length of the second line are determined using one or more images of the leg;
using the first angle, determining an alignment measurement of the leg; and
displaying the alignment measurement of the leg on a display.

2. The method of claim 1, wherein the measurement system is included in a prosthetic component.

3. The method of claim 1, wherein the tibial stem is inserted into an opening drilled in the tibia.

4. The method of claim 1, wherein determining the alignment measurement of the leg includes using the first angle to calculate a frontal plane knee angle of the leg.

5. The method of claim 4, further comprising, using the measurement data corresponding to the at least one first movement, determining a sagittal plane knee angle of the leg.

6. The method of claim 5, further comprising displaying at least one of the frontal plane knee angle and the sagittal plane knee angle on the display.

7. The method of claim 4, further comprising:
moving the leg through at least one second movement;
generating measurement data corresponding to the at least one second movement via the measurement system; and
using the measurement data corresponding to the at least one second movement, determining a transverse plane knee angle of the leg.

8. The method of claim 7, further comprising displaying at least one of the frontal plane knee angle and the transverse plane knee angle on the display.

9. The method of claim 7, wherein the at least one first movement includes rotating the leg about a joint line of the leg and wherein the at least one second movement includes rotating a tibia of the leg relative to a femur of the leg.

10. A method of measuring leg alignment, comprising:
moving a leg through at least one movement;
generating measurement data corresponding to the at least one movement via a measurement system coupled to the leg;
obtaining a measured length of a bone of the leg;
using the measurement data corresponding to the at least one first movement and the measured length of the bone, determining an alignment measurement of the leg; and
displaying the alignment measurement of the leg on a display.

11. The method of claim 10, wherein the bone of the leg is a tibia.

12. The method of claim 10, wherein the bone of the leg is a femur.

13. The method of claim 10, further comprising:
using the measurement data corresponding to the at least one first movement and the measured length of the bone, determining a first angle included in a triangle formed by a first line extending from a hip joint of the leg to a knee joint of the leg, a second line extending from the knee joint to an ankle joint of the leg, and a third line extending from the hip joint to the ankle joint; and
using the first angle, determining the alignment measurement of the leg, wherein the alignment measurement of the leg is a frontal knee plane angle of the leg.

14. The method of claim 10, wherein the at least one first movement includes rotating the leg about a joint line of the leg.

15. A method of measuring leg alignment, comprising:
moving a leg through at least one first movement including rotating the leg about a joint line of the leg;
generating measurement data corresponding to the at least one first movement via a measurement system included in a permanent prosthetic knee joint coupled to the leg;

using the measurement data corresponding to the at least one first movement, determining a first alignment measurement of the leg, wherein the first alignment measurement is a sagittal plane knee angle; and displaying the first alignment measurement of the leg on a display.

16. The method of claim 15, further comprising:

moving the leg through at least one second movement;

generating measurement data corresponding to the at least one second movement via the measurement system included in the prosthetic knee joint coupled to the leg;

using the measurement data corresponding to the at least one second movement, determining a second alignment measurement of the leg; and displaying the first alignment measurement of the leg and the second alignment measurement of the leg on the display.

17. The method of claim 16, wherein the at least one second movement includes rotating a tibia of the leg relative to a femur of the leg and wherein the second alignment measurement is a transverse plane knee angle.

18. The method of claim 15, wherein the first alignment measurement is indicative of an alignment of a femur of the leg relative to a mechanical axis of the leg or an alignment of a tibia of the leg to the mechanical axis of the leg.

* * * * *